United States Patent [19]
Kleiner et al.

[11] Patent Number: 4,948,918
[45] Date of Patent: Aug. 14, 1990

[54] PROCESS FOR THE PREPARATION OF α-AMINOALKYLPHOSPHONIC ACIDS

[75] Inventors: Hans-Jerg Kleiner, Kronberg/Taunus; Günter Bartels, Brunswick, both of Fed. Rep. of Germany

[73] Assignee: Hoechst Aktiengesellschaft, Frankfurt am Main, Fed. Rep. of Germany

[21] Appl. No.: 373,329

[22] Filed: Jun. 29, 1989

Related U.S. Application Data

[63] Continuation of Ser. No. 36,489, Apr. 9, 1987, abandoned.

[30] Foreign Application Priority Data

Apr. 11, 1986 [DE] Fed. Rep. of Germany ....... 3612192

[51] Int. Cl.$^5$ .............................................. C07F 9/38
[52] U.S. Cl. ................................. 562/16; 558/170; 556/405
[58] Field of Search ......................................... 562/16

[56] References Cited

PUBLICATIONS

Wallis et al., "The Hofmann Reaction" in *Organic Reactions*, vol. III, Ed. R. Adams et al., John Wiley & Sons, 1946, pp. 267–306.
Rachon et al., Chem. Abstracts 81 63728m, p. 484 (1974).
Rachon et al., Z. Chem., 14, No. 4, pp. 152–154 (1974).
The Merck Index, Eighth Edition (1968), p. 1179.
Maier, L., "Advances in the Chemistry of Aminophosphinic Acids", *Phosphorus and Sulfur* 14, 295–322 (1983).
Soroka, M. et al., *Tetrahedron Letters* 52, 5201–5202 (1973).
Speziale, A. J. et al., *J. Org. Chem.* 23, 1883–1886 (1958).

*Primary Examiner*—J. E. Evans

[57] ABSTRACT

A process for the production of α-aminoalkylphosphonic acids or salts thereof of the formula A

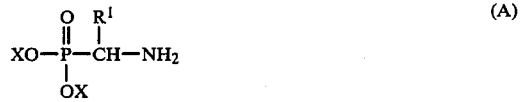

wherein $R^1$ represents hydrogen, alkyl having from 1 to 4 carbon atoms or $CH_2-C_6H_5$ and X hydrogen or a metal cation, which comprises reacting a compound of the formula B

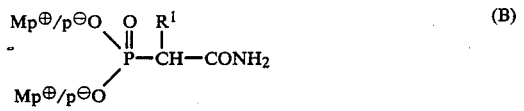

in which $R^1$ has the same meaning as in formula A and $Mp^\oplus$ represents hydrogen or a p-valent metal cation, with a hypohalite of a p-valent metal cation, and isolating the metal salt produced or acidifying the reaction mixture obtained to produce the α-aminoalkyl-phosphonic acid.

18 Claims, No Drawings

PROCESS FOR THE PREPARATION OF α-AMINOALKYLPHOSPHONIC ACIDS

This application is a continuation of our copending application Ser. No. 07/036,489, filed Apr. 9, 1987, and now abandoned.

Unsubstituted aminomethylphosphonic acid of the formula A (see patent claim 1) (each of $R_1$ and $X=H$) and various similar phosphorus-containing compounds have a biological-mainly a herbicidal—activity; some of the compounds can also be further processed into biologically active substances—cf. the article by L. Maier "Advances in the Chemistry of Aminophosphinic Acids" in the journal "Phosphorus and Sulfur" 1983 Vol. 14, pp. 295-322, in particular 317-320. Although this article is concerned mainly-as can be seen from the title—with aminophosphinic acids, aminophosphonic acids are also dealt with.

For this reason, part A—Preparation of aminophosphinic acids—on pages 296-315 of this article describes not only a number of known processes for the preparation of aminophosphinic acids, but also various methods for the preparation of aminophosphonic acids. The compounds of the formula A can, in principle, also be obtained by these processes.

One method which is not described in the article mentioned is the process, described in the work by M. Soroka and P. Mastalerz "Hofmann Degradation and Bromination of Amides derived from Phosphonoacetic Acid" (Tetrahedron Letters No. 52, pp. 5201-5202, 1973), for the preparation of some specific α-aminoalkylphosphonic acids by the Hofmann degradation and acid hydrolysis of the esters of various phosphonocarboxamides.

The Hofmann degradation can also be used to convert carboxamides into amines containing one carbon atom fewer by treatment with chlorine or bromine in alkaline medium (in which the corresponding hypohalites form) (cf., for example, Organic Reactions 3 (1946), pp. 267 ff. "The Hofmann Reaction", in particular p. 268); the following reaction equation (with bromine as halogen and with R denoting an organic radical) is given for the Hofmann degradation:

$$RCONH_2 + Br_2 + 4OH^- \rightarrow R-NH_2 + CO_3^{2-} + 2Br^- + 2H_2O$$

The Hofmann degradation reactions described in the work by M. Soroka and P. Mastalerz, in loco citato, can be illustrated by the following equation:

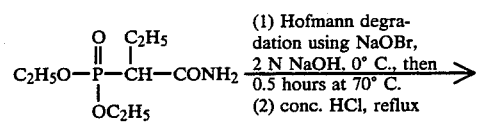
(1) Hofmann degradation using NaOBr, 2 N NaOH, 0° C., then 0.5 hours at 70° C.
(2) conc. HCl, reflux
(a)

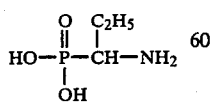

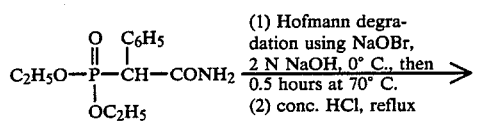
(1) Hofmann degradation using NaOBr, 2 N NaOH, 0° C., then 0.5 hours at 70° C.
(2) conc. HCl, reflux
(b)

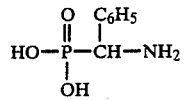

The yields of the appropriate α-aminoalkylphosphonic acids are said to be 70 to 80% of theory.

If the carbon atom bonded to phosphorus is unsubstituted or substituted by other groups, primarily halogen-substituted phosphonocarboxylic acid derivatives (and virtually no halogen-free amines) are produced under the conditions of the Hofmann degradation, as can be seen from equations c), d) and e).

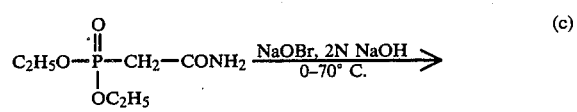 (c)

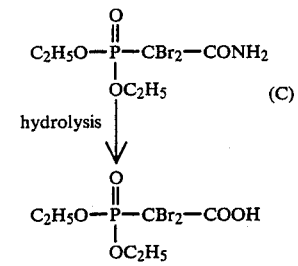
(C)

If 2 moles of NaOBr are used in place of the one mole which is otherwise conventional for the Hofmann degradation, the yield of the compound diethyl aminocarbonyldibromomethylphosphonate C is up to 75%.

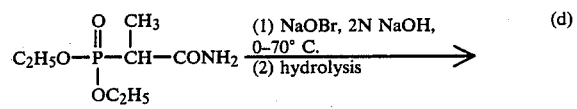 (d)

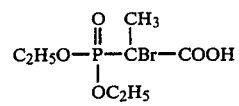

(yield: 70%)

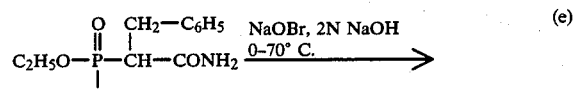 (e)

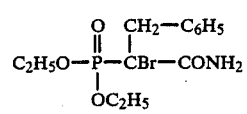

(yield: 80%)

In the final product of reaction (e), the $CONH_2$ group can also be hydrolyzed into the hydroxyl group. If the hydrolysis is continued further, the phosphonate groups in this acid, and in those from reactions (c) and (d), are also hydrolyzed into OH groups.

As our own experiments have shown, virtually no halogenfree amine of the formula A, where $R_1=H$, is produced either in the abovementioned reaction when the NaOBr is replaced by NaOCl.

In attempting to modify the reactions described by M. Soroka and P. Mastalerz, in loco citato—illustrated under (c), (d) and (e) above—in a fashion such that the normal halogen-free Hofmann degradation products ($\alpha$-aminoalkylphosphonic acids) are also produced in high yields, and in attempting to extend this reaction, if appropriate, to other similar phosphorus/carbon compounds, it has already been proposed that the synthesis is started not from the esters of the corresponding aminocarbonylalkylphosphonic acids (M. Soroka and P. Mastalerz, in loco citato), but instead from the respective ester salts—and in the aminocarbonylalkylphosphinic acid series, in an analogous fashion from aminocarbonylalkylphosphinic acid salts (European Published Specification No. 184,753 corresponding to South African Patent No. 85/9481).

The abovementioned patent relates to a process for the preparation of $\alpha$-aminoalkylphosphonic and $\alpha$-aminoalkylphosphinic acids of the formula I

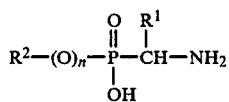  (I)

in which n denotes 1 or 0, $R^1$ denotes H, $CH_3$ or $CH_2$—$C_6H_5$, and $R_2$ denotes H (for n=1) and alkyl or phenyl (for n=0), wherein compounds of the formula II

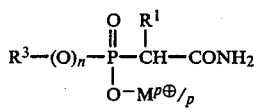  (II)

in which n and $R_1$ have the same meaning as in the formula I, and $R^3$ denotes alkyl (for n=1), and alkyl or phenyl (for n=0), and $M^{p\oplus}$ denotes a p-valent cation, are subjected to a Hofmann degradation, and the compounds of the formula I are obtained in a known fashion. In this reaction, the $\alpha$-aminoalkylphosphonic and $\alpha$-aminoalkylphosphinic acids of the formula I are consistently obtained in yields between about 70 and 90% of theory.

In further developing this process, it has now been found that the $\alpha$-aminoalkylphosphonic acids can advantageously also be obtained by Hofmann degradation of the appropriate aminocarbonylalkylphosphonic acid (full) salts (instead of the ester salts) by the process of the abovementioned patent. The invention therefore relates to a process for the preparation of $\alpha$-aminoalkylphosphonic acids, or the salts thereof, of the formula A (see patent claim 1), in which $R^1$ is H, alkyl having 1–4 carbon atoms or $CH_2$—$C_6H_5$, and X is H or a metal cation, wherein salts of the aminocarbonylphosphonic acid of the formula B (see patent claim 1), in which $R^1$ has the same meaning as in the formula A, and $M^{p\oplus}$ or a p-valent metal cation, preferably $Na^\oplus$ or $K^\oplus$ are subjected to a Hofmann degradation, that is to say are treated with a hypohalite of a p-valent metal cation, and the metal salt formed is isolated or the resultant reaction mixture is acidified for preparation of the $\alpha$-aminoalkylphosphonic acid. The alkyl radical of $R^1$ can be methyl, ethyl, propyl, isopropyl, n-butyl, sec.-butyl, t-butyl or isobutyl, and is preferably methyl. However, $R^1$ is particularly preferably hydrogen. The reaction according to the invention is expediently carried out at temperatures between 20 and 90° C.

From the salts thus obtained, the $\alpha$-aminoalkylphosphonic acids of the formula A can be obtained in a conventional fashion.

The yields in the process according to the invention are in the same order of magnitude as those according to the process of the abovementioned patent. This is very surprising since, according to M. Soroka and P. Mastalerz and according to our own experiments mentioned above, mainly halogenated phosphonic acid derivatives, and virtually no normal halogen-free Hofmann degradation products (amines) are obtained by Hofmann degradation and acid hydrolysis of the compounds of the formula B in fully-esterified form. The completely different course of the reaction—according to the invention—could not be expected as a consequence of the relatively minor modification of the starting materials (salts in place of esters).

The starting materials for the process according to the invention—i.e. the aminocarbonylalkylphosphonic acid salts of the formula B—can be obtained by known processes. Firstly, the dialkyl aminocarbonylalkylphosphonates are prepared, for example by reacting phosphorous acid esters with $\alpha$-halocarboxamides (for example corresponding to J. Org. Chem. 23, pp. 1883–1886 (1958)), and converting these, expediently by means of trimethylsilyl bromide, into bis-trimethylsilyl esters; the latter can easily be hydrolyzed using water. The aminocarbonylalkylphosphonic acids formed in this process must then be neutralized. This preparation process can be illustrated by the following equations:

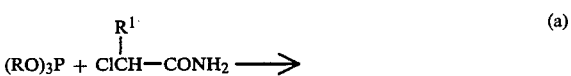  (a)

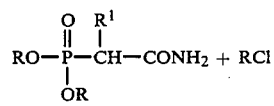

(R = alkyl)

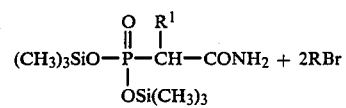  (b)

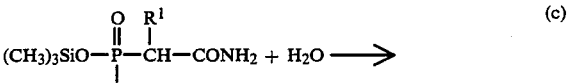

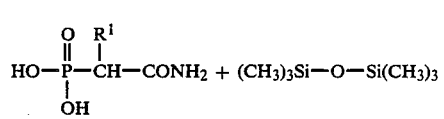  (c)

Hexamethyl disiloxane $(CH_3)_3Si-O-Si(CH_3)_3$ can be reconverted into trimethylsilyl bromide $(CH_3)_3SiBr$ using $PBr_3$.

The Hofmann degradation of the compounds of the formula B is carried out, for example, using chlorine or bromine and alkali metal hydroxide solution, in particular NaOH or KOH, as is conventional and known for this type of reaction. In this reaction, a procedure is preferably followed in which, by reacting chlorine or bromine in an alkali metal hydroxide solution, an alkaline hypohalite solution is initially prepared. The compound B is introduced into this solution, either in solid form or as an aqueous solution, expediently at about 20 to 30° C. Of course, it is also possible to employ, for example, the free aminocarbonylalkylphosphoriic acid or alternatively the monosalts thereof, just as long as the hypohalite solution is sufficiently alkaline. Salts of the formula B then form in the solution. The halogen:alkali metal hydroxide:compound B molar ratio is, for example, about (1 to 1.2):about (4 to 6):about 1.

After adding the compound B or the corresponding free aminocarbonylmethylphosphonic acid, the temperature is advantageously increased to about 90° C., preferably 40 to 80° C., and in particular to about 60 to 75° C. An exothermic reaction usually sets in here, particularly from about 50° C., so that cooling is then necessary, if appropriate.

The resultant reaction solution is worked up in a conventional fashion. For example, a reaction with acids—for example with hydrochloric acid—is carried out in order to liberate the α-aminoalkylphosphonic acid (A). The solution is then concentrated by evaporation, and the major part of the inorganic salts is deposited. The resulting solution can be used, if desired, for further reactions. It is also possible to concentrate the solution to dryness under reduced pressure and to obtain substantially pure aminoalkylphosphonic acid A with the aid of suitable solvents, such as CH₃OH, HCOOH, CH₃COOH etc. For further purification, the product can be recrystallized.

The invention is now illustrated in greater detail by the following example. After the example of the invention, a comparison example follows from which can be seen that virtually no aminomethanephosphonic acid is produced from diethyl aminocarbonylmethylphosphonate under the conditions of the Hofmann degradation.

EXAMPLE

Aminomethanephosphonic acid

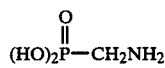

(a) Preparation of the starting material Na salt of aminocarbonylmethylphosphonic acid

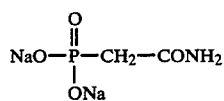

Diethyl aminocarbonylmethylphosphonate was obtained in a known fashion according to Arbusov from triethylphosphite and chloroacetamide.

The diethyl ester was then converted into the bis-trimethylsilyl ester using trimethylsilyl bromide. To this purpose, 306 g (2 mol) of trimethylsilyl bromide were added dropwise, with stirring, to a solution of 195 g (1 mol) of diethyl aminocarbonylmethylphosphonate in 300 g of dichloromethane. The temperature increased to 40° C. during this addition. The mixture was stirred for a further 5 hours, and the volatile components were removed by distillation in a water-pump vacuum to an internal temperature of 60° C. The residue was 283 g of bistrimethylsilyl aminocarbonylmethylphosphonate (yield 100% of theory). The product crystallized.

Hydrolysis of the bis-trimethylsilyl ester:

283 g (1 mol) of bis-trimethylsilyl aminocarbonylmethylphosphonate were warmed to about 70° C. and, in the thus liquefied form, added dropwise to 100 ml of water at 20° C. with stirring and cooling. The mixture was then cooled to 0° C When the crystallization was complete, the crystals were filtered off under suction. 118 g of aminocarbonylmethylphosphonate were obtained. The filtrate comprised two layers; the upper layer was separated off (hexamethyl disiloxane) and the lower layer was concentrated; a further 12 g of product were obtained from this. In total, 130 g of aminocarbonylmethylphosphonic acid, melting point 178–180° C., were obtained. This corresponds to a yield of 93.5% of theory.

$C_2H_6NO_4P$

MW: 139 calc.: 17.25% C, 4.32% H, 10.06% N, 22.3% P, found: 17.0% C, 4.4% H, 9.9% N, 22.3% P.

Neutralization of the free aminocarbonylmethylphosphonic acid:

56 g (0.4 mol) of aminocarbonylmethylphosphonic acid were dispersed in water. Concentrated sodium hydroxide solution was added dropwise to this dispersion with cooling until a clear solution of pH 6.5 had been produced. 145 g of such a solution were obtained.

(b) Reaction according to the invention

The solution—prepared as described above—was run into a hypochlorite solution, prepared at −5° C. from 67.2 g (1.68 mol) of sodium hydroxide, 29.8 g (0.42 mol) of chlorine and 400 ml of water, at 30° C. for 5 minutes. The temperature increased to 50° C., then within a minute to 80° C.; the mixture was cooled. The reaction mixture was then kept at 70° C. for about 30 minutes. The mixture was then cooled, and the pH was adjusted to 2.6 by passing in hydrogen chloride. The mixture was then concentrated almost to dryness in a water-pump vacuum, and the residue was stirred with 100 ml of concentrated hydrochloric acid, filtered off under suction and rinsed with concentrated hydrochloric acid. 124 g of sodium chloride were filtered off under suction. The filtrate was concentrated, treated with water, and again evaporated to dryness, finally in a high vacuum at a bath temperature of 70° C. The resulting residue was digested with methanol/water. A total of 31 g of aminomethanephosphonfc acid were obtained. This corresponds to a yield of 70% of theory.

COMPARISON EXAMPLE

Attempted Hofmann degradation of diethyl aminocarbonylmethylphosphonate

78 g (0.4 mol) of diethyl aminocarbonylmethylphosphonate were added at room temperature to a hypochlorite solution prepared at 0° C from 67.2 g (1.68 mol) of sodium hydroxide, 29.8 g (0.42 mol) of chlorine and 400 ml of water.

The reaction solution, which initially warmed to 50° C. without heating, was heated at 65° C. for 30 minutes and, after cooling, acidified using concentrated hydrochloric acid. After evaporation in a rotary evaporator, 150 ml of concentrated hydrochloric acid were added, the sodium chloride formed was filtered off, and the filtrate was refluxed for 2 hours. After exhaustive evaporation, 200 ml of methanol and 30 ml of pyridine were added. No precipitation of aminomethanephosphonic acid, which is insoluble under these conditions, was noticed. In addition, only traces of aminomethanephosphonic acid could be detected on a thin-layer chromatogram.

I claim:

1. A process for the production of α-aminoalkylphosphonic acid or salts thereof of the formula A

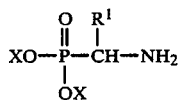
(A)

wherein $R^1$ represents hydrogen, and X hydrogen or a metal cation, which comprises reacting a compound of the formula B

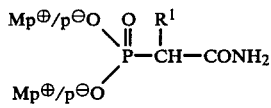
(B)

in which $R^1$ has the same meaning as in formula A and $Mp^{\oplus}$ represents hydrogen or a p-valent metal cation, with a hypohalite of a p-valent metal cation, and isolating the metal salt produced or acidifying the reaction mixture obtained to produce the α-aminoalkyl-phosphonic acid.

2. A process as claimed in claim 1, wherein the hypohalite is hypobromite o hypochlorite.

3. A process as claimed in claim 1, wherein compound B is reacted with chlorine or bromine and an aqueous alkali hydroxide solution.

4. A process as claimed in claim 1, wherein the reaction is carried out at a temperature in the range from about 20 to 90° C.

5. A process as claimed in claim 3, wherein the reaction is carried out at a temperature in the range from 40 to 80° C.

6. A process as claimed in claim 4, wherein the reaction is carried out at a temperature in the range from 60 to 75° C.

7. A process as claimed in claim 3, wherein the molar ratio of halogen: alkali hydroxide:compound B is in the range from about (1 to 1.2):about(4 to 6):about 1.

8. A process as claimed in claim 1, wherein M is Na or K.

9. A process for the production of α-aminoalkylphosphonic acids or salts thereof of the formula A

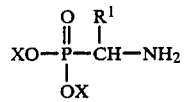
(A)

wherein $R^1$ represents hydrogen, $CH_3$ or $CH_2-C_6H_5$ and X hydrogen or a metal cation, which comprises reacting a compound of the formula B

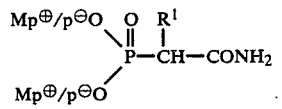
(B)

in which $R^1$ has the same meaning as in formula A and $Mp^{\oplus}$ repreeente hydrogen or a p-valent metal cation, with a hypochorlite of a p-valent metal cation, and isolating the metal salt produced or acidifying the reaction mixture obtained to produce the α-aminoalkylphosphonic acid.

10. A process as claimed in claim 9, wherein compound B is reacted with chlorine and an aqueous alkali hydroxide solution.

11. A process as claimed in claim 9, wherein the reaction is carried out at a temperature in the range from about 20 to 90° C.

12. A process as claimed in claim 9, wherein the reaction is carried out at a temperature in the range from 40 to 80° C.

13. A process as claimed in claim 9, wherein the reaction is carried out at a temperature in the range from 60 to 75° C.

14. A process as claimed in claim 10, wherein the molar ratio of chlorine: alkali hydroxide:compound B is in the range from about (1 to 1.2):about(4 to 6):about 1.

15. A process as claimed in claim 9, wherein M is Na or K.

16. A process as claimed in claim 9, wherein X is hydrogen.

17. A process for the production of α-aminoalkylphosphonic acids or salts thereof of the formula A

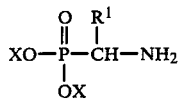
(A)

wherein $R^1$ represents $CH_3$ and X hydrogen or a metal cation, which comprises reacting a compound of the formula B

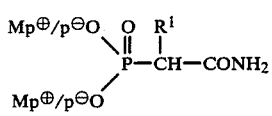
(B)

in which $R^1$ has the same meaning as in formula A and $Mp^{\oplus}$ represents hydrogen or a p-valent metal cation, with a hypochlorite of an alkali metal, and isolating the metal salt produced or acidifying the reaction mixture obtained to produce the α-aminoalkyl-phosphonic acid.

18. A process as claimed in claim 9, wherein compound B is reacted with chlorine and an aqueous sodium hydroxide solution.

* * * * *

UNITED STATES PATENT AND TRADEMARK OFFICE
CERTIFICATE OF CORRECTION

PATENT NO. : 4,948,918

DATED : 8/14/90

INVENTOR(S) : Hans-Jerg Kleiner et al

It is certified that error appears in the above-identified patent and that said Letters Patent is hereby corrected as shown below:

In claim 9, column 8, line 18, "represente" should read --represents--.

Signed and Sealed this

Third Day of December, 1991

Attest:

HARRY F. MANBECK, JR.

*Attesting Officer*      *Commissioner of Patents and Trademarks*